US011298237B2

United States Patent
Starker et al.

(10) Patent No.: US 11,298,237 B2
(45) Date of Patent: Apr. 12, 2022

(54) SPACER UNIT FOR USE IN A MOVABLE JOINT OF A PROSTHETIC OR ORTHOPEDIC SYSTEM

(71) Applicant: Ossur Iceland ehf, Reykjavik (IS)

(72) Inventors: Felix Starker, Reykjavik (IS); Bjarni Andresson, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 362 days.

(21) Appl. No.: 16/384,318

(22) Filed: Apr. 15, 2019

(65) Prior Publication Data
US 2019/0336296 A1 Nov. 7, 2019

Related U.S. Application Data

(60) Provisional application No. 62/666,873, filed on May 4, 2018.

(51) Int. Cl.
*A61F 2/38* (2006.01)
*A61F 2/32* (2006.01)
*A61F 2/30* (2006.01)

(52) U.S. Cl.
CPC ...... *A61F 2/38* (2013.01); *A61F 2002/30329* (2013.01)

(58) Field of Classification Search
CPC .................. A61F 2/30; A61F 2/32; A61F 2/38
See application file for complete search history.

(56) References Cited

U.S. PATENT DOCUMENTS

| 5,443,527 | A | 8/1995 | Wilson |
| 5,545,234 | A | 8/1996 | Collier, Jr. |
| 5,800,563 | A * | 9/1998 | Arbogast ............ A61F 2/76 623/35 |
| 5,899,944 | A | 5/1999 | Phillips |
| 5,961,556 | A | 10/1999 | Thorn |
| 6,129,766 | A | 10/2000 | Johnson et al. |
| 6,280,479 | B1 | 8/2001 | Phillips |
| 6,290,730 | B1 | 9/2001 | Pitkin et al. |
| 6,296,669 | B1 | 10/2001 | Thorn et al. |
| 6,402,789 | B1 | 6/2002 | Gramnäs |
| 6,468,315 | B1 | 10/2002 | Wilkinson et al. |
| 6,511,512 | B2 | 1/2003 | Phillips et al. |
| 6,699,295 | B2 | 3/2004 | Lee et al. |

(Continued)

FOREIGN PATENT DOCUMENTS

GB          2305363 A          4/1997

OTHER PUBLICATIONS

International Search Report from PCT Application No. PCT/US2019/027449, dated Jul. 31, 2019.

*Primary Examiner* — Jason-Dennis N Stewart
(74) *Attorney, Agent, or Firm* — Workman Nydegger

(57) ABSTRACT

A prosthetic system includes a movable joint defining at least one gap, and at least one spacer unit positionable in the at least one gap. The at least one spacer unit includes a resilient element that is controllably deformable to vary a thickness of the at least one spacer unit to fill the at least one gap, and to reduce the likelihood of the at least one spacer unit interfering with relative movement between components of the movable joint. The at least one material forming the resilient element is compressible in a first direction with little or no expansion in a second direction normal to the first direction.

15 Claims, 6 Drawing Sheets

(56) References Cited

U.S. PATENT DOCUMENTS

| | | | |
|---|---|---|---|
| 6,764,521 B2 | 7/2004 | Molino et al. | |
| 6,887,279 B2 | 5/2005 | Phillips et al. | |
| 7,896,927 B2 | 3/2011 | Clausen et al. | |
| 9,387,096 B2 | 7/2016 | Sverrisson et al. | |
| 9,561,118 B2 | 2/2017 | Clausen et al. | |
| 2005/0261783 A1 | 11/2005 | Geilman et al. | |
| 2009/0105758 A1 | 4/2009 | Gimbel et al. | |
| 2010/0030335 A1 | 2/2010 | Arramon | |
| 2010/0042228 A1 | 2/2010 | Doddroe et al. | |
| 2011/0118845 A1 | 5/2011 | Overes et al. | |
| 2011/0202139 A1 | 8/2011 | Metzger et al. | |
| 2013/0066439 A1 | 3/2013 | Zamora et al. | |
| 2016/0009523 A1 | 1/2016 | Omarsson et al. | |
| 2016/0256285 A1* | 9/2016 | Jansen | A61F 2/3872 |
| 2018/0036145 A1 | 2/2018 | Jury et al. | |
| 2020/0214684 A1* | 7/2020 | Mcauliffe | A61F 2/461 |

\* cited by examiner

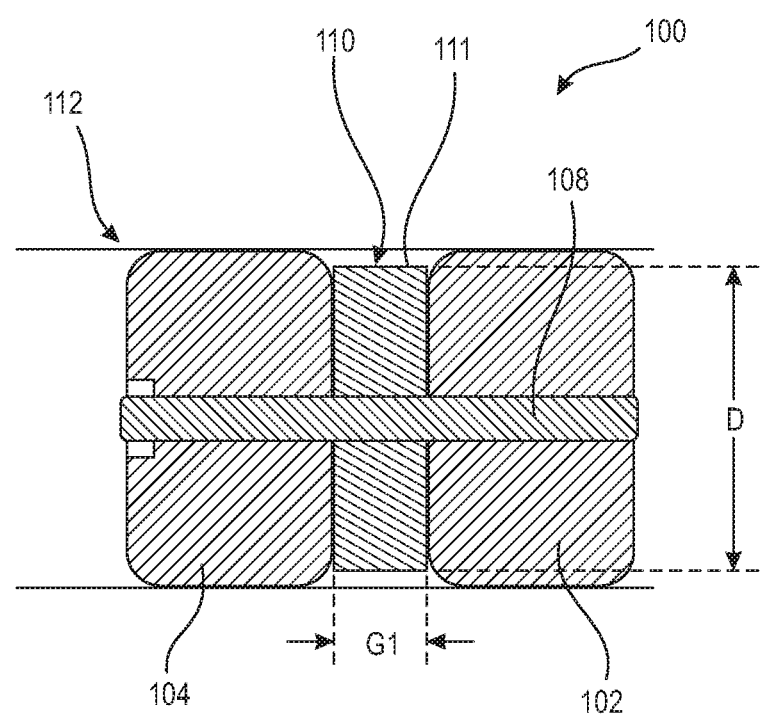
FIG. 3
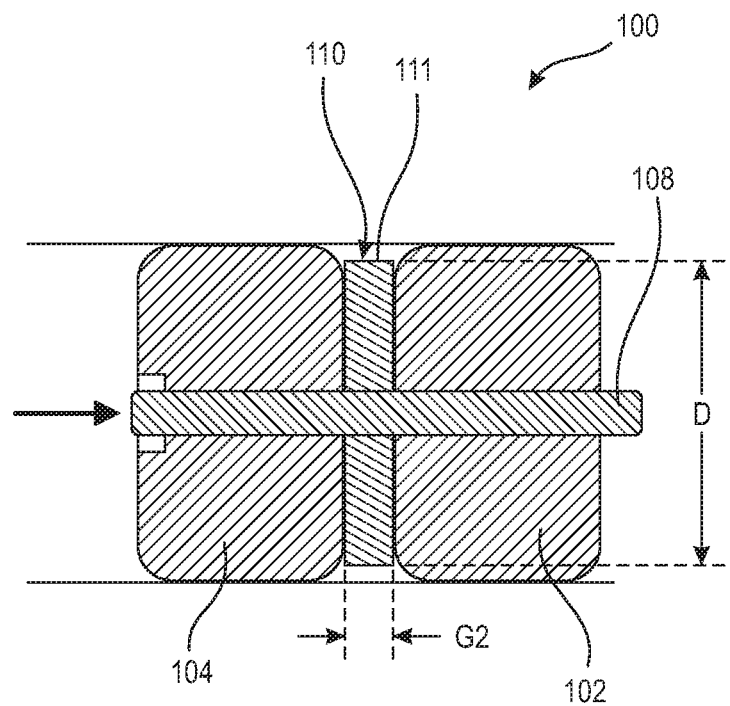

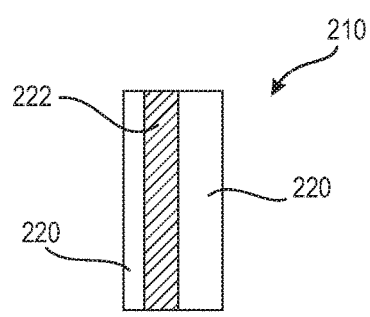
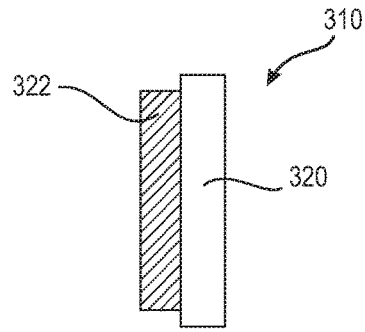
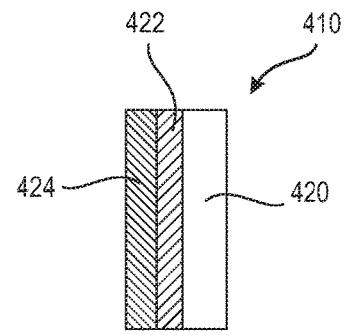
FIG. 4　　　　　　FIG. 5　　　　　　FIG. 6
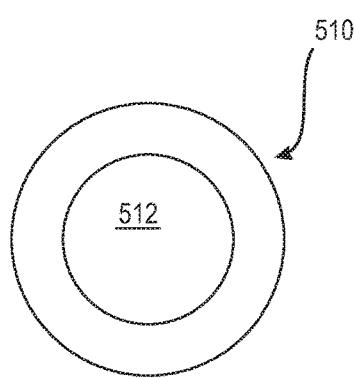
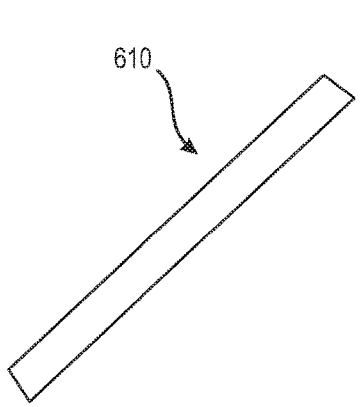
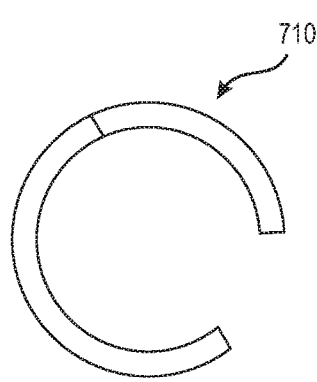
FIG. 7　　　　　　FIG. 8　　　　　　FIG. 9

SPACER UNIT FOR USE IN A MOVABLE JOINT OF A PROSTHETIC OR ORTHOPEDIC SYSTEM

TECHNICAL FIELD

The disclosure pertains to components used in joints of prosthetic and/or orthopedic systems.

BACKGROUND

Many conventional orthopedic and prosthetic systems require at least one movable joint for controlling, supporting, immobilizing, replacing, or treating muscles, joints, or skeletal parts, which are weak, ineffective, deformed, missing, or injured. Movable joints are generally designed to allow relative movement between components of a system in one or more degrees of freedom, and restrict movement in one or more others (e.g., a pivot point, an axle connection, a sliding connection). Such movable joints can be found in prosthetic knees, prosthetic feet, prosthetic shock absorbers, and many other types of prosthetic and orthopedic systems.

Usually a gap is present between the components forming the movable joint that receives a metal or plastic washer. This gap unfortunately is known to vary in size because of manufacturing differences in the components (e.g., +/− about 0.5 mm). Also, washer size regularly varies from one washer to another. These types of inconsistencies from movable joint to movable joint and washer to washer can be problematic for many reasons. For instance, if the gap is too small or the washer is too big, the washer may require permanent alterations such as grinding or cutting to fit the washer in the gap. If the gap is too big or the washer is too small, additional washers of varying sizes may be required and/or permanent alterations of the washers may be required to effectively bring the fit of the washers in the gap within acceptable tolerances.

Modifying washers (e.g., via grinding) and custom fitting different numbers of washers between the components are labor-intensive and time-consuming activities prone to inconsistencies and error. In addition, contact between the components and a metal or plastic washer during movement of the movable joint may produce an undesirable stick-slip effect and/or sudden movements in the movable joint, negatively impacting the performance of the movable joint and increasing the likelihood of injury or patient dissatisfaction.

There is thus a need to simplify the assembly of movable joints in prosthetic and orthopedic systems and to improve their performance.

SUMMARY

The disclosure describes various embodiments of a spacer unit for use in a movable joint of a prosthetic or orthopedic system which overcomes the problems mentioned above by reducing free play, providing axial and radial damping, and facilitating easier assembly.

According to an embodiment, a spacer unit is positionable in a gap defined within a movable joint. The spacer unit includes a resilient element formed of at least one material that is controllably deformable to vary a thickness of the at least one spacer unit to fill the at least one gap. The at least one material can be compressible in a first direction with little or no expansion in a second direction normal to the first direction. This helps to avoid the potential drawbacks of the resilient element expanding radially under compression and interfering with the proper movement of the movable joint. It also helps to quickly and easily fit the spacer unit in the gap, facilitating assembly of the movable joint. This is advantageous over known movable joints as rigid washers customarily positioned in gaps tend to vary in size because of manufacturing imperfections, resulting often in the costly and labor-intensive process of grinding excess material from the washers, or adding additional washers to fill the gap.

In addition, the controlled deformation of the resilient element can provide an axial resistance within the gap to help space components of the movable joint. It can also dynamically reduce axial play between the components during use of the movable joint as the thickness of the spacer unit changes with the size of the gap while helping to maintain the components apart. The resilient element also can provide an amount of torsional damping as the components rotate relative to one another, making the operation of the movable joint feel more natural or smooth. Moreover, deformation of the resilient element within the gap can help absorb energy if lateral or medial forces are generated in the movable joint, offering an amount of axial damping.

Further, the resilient element may also help to reduce and mitigate stick/slip effects between metal components and reduce "free play" effects between components of the movable joint.

According to a variation, the spacer unit includes at least one rigid element that forms a bearing surface between the spacer unit and the movable joint. This beneficially allows the spacer unit to compress and distribute loads in the gap while the at least one rigid element directs forces away from the resilient element, reducing wear and tear on the spacer unit. The at least one rigid element may be formed of metal and/or a plastic material that helps direct forces away from the resilient element and allows the resilient element to compress and absorb differences or changes in the size of the gap.

According to other embodiments of the spacer unit, spacer units may comprise numerous variations and configurations of rigid elements arranged with resilient elements to provide damping, force distribution, operational advantages, and easier assembly in different prosthetic and orthopedic devices.

BRIEF DESCRIPTION OF THE DRAWINGS

These and other features, aspects, and advantages of the present disclosure will become better understood regarding the following description, appended claims, and accompanying drawings.

FIG. 3 is a schematic cross section of the movable joint in FIG. 1 in a loaded and unloaded configuration.

FIG. 4 is a schematic cross-section of a spacer unit according to another embodiment.

FIG. 5 is a schematic cross-section of a spacer unit according to another embodiment.

FIG. 6 is a schematic cross-section of a spacer unit according to another embodiment.

FIG. 7 is a side view of a spacer unit according to another embodiment.

FIG. 8 is a side view of a spacer unit according to another embodiment.

FIG. 9 is a side view of a spacer unit according to another embodiment.

DETAILED DESCRIPTION OF VARIOUS EMBODIMENTS

Figure 1:
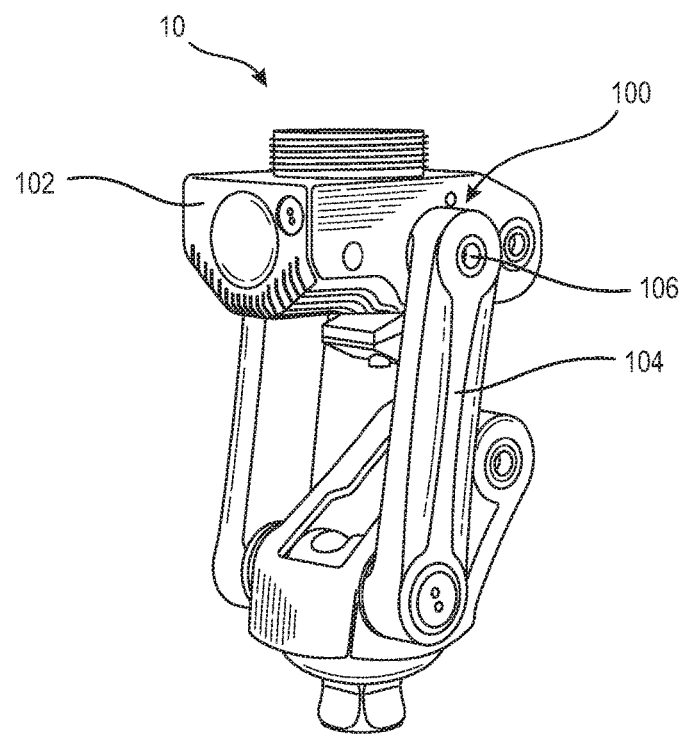
FIG. 1 is a perspective view of a prosthetic device including a movable joint according to an embodiment.

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the specific embodiments disclosed, but on the contrary, the aim covers all modifications, alternative constructions, combinations, and equivalents falling within the spirit and scope of the disclosure.

It will be understood that unless a term is expressly defined in this application to possess a described meaning, there is no intent to limit the meaning of such term, either expressly or indirectly, beyond its plain or ordinary meaning. Any element in a claim that does not explicitly state "means for" performing a specified function, or "step for" performing a specific function is not to be interpreted as a "means" or "step" clause as specified in 35 U.S.C. § 112(f).

Embodiments of the present disclosure include a spacer unit for use with a movable joint that simplifies assembly of a movable joint in a prosthetic or orthopedic system and can improve its performance. The spacer unit includes a resilient element formed of at least one material that is controllably deformable within a gap defined within the movable joint to effectively fill the gap. The at least one material can be compressible in a first direction with little or no expansion in a second direction normal to the first direction. This can provide an axial resistance within the gap arranged to help space components of the movable joint, reducing axial play between the components of the movable joint and the reducing likelihood of the spacer unit interfering with relative movement between components of the movable joint. The resilient element can also dynamically reduce axial play between the components during use of the movable joint as the thickness of the spacer unit changes with the size of the gap while helping to maintain the components apart. Moreover, deformation of the resilient element within the gap can absorb energy if lateral or medial forces are generated in the movable joint, offering an amount of axial damping. It also can provide an amount of torsional damping as the components rotated relative to one another, making the movement of the movable joint feel more natural or smooth.

The spacer unit embodiments described are configured for use with movable joints including a prosthetic knee, a prosthetic foot, a prosthetic shock absorber, and a bearing for a prosthetic device. It should be remembered, however, that the same concepts and methods described may be similarly used for other prosthetic and orthopedic systems.

As shown in FIG. 1, embodiments of the spacer unit can be employed with at least one movable joint 100 of a prosthetic system 10. The prosthetic system 10 is shown as a prosthetic knee but can be any suitable prosthetic or orthopedic system. The movable joint 100 can include first and second components 102, 104 which are arranged to rotate relative to one another about at least one pivot point 106. It will be appreciated that both or one of the components 102, 104 may be arranged to rotate about the pivot point 106. The pivot point 106 is shown being defined by an axle 108 extending through the first and second components 102, 104.

Figure 2:
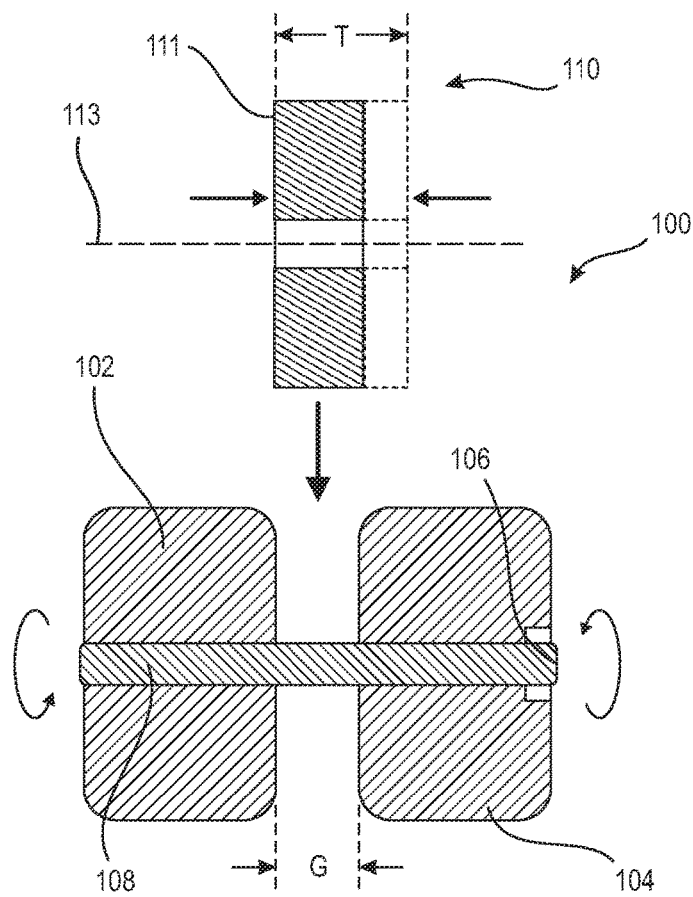
FIG. 2 is a schematic cross section of the movable joint in FIG. 1.

FIG. 2 is a schematic cross section of the movable joint 100 of FIG. 1. A gap G is defined between the first component 102 and the second component 104 along a length of the axle 108. A spacer unit 110 is received in the gap G between the first and second parts 102, 104. The spacer unit 110 includes a body having a resilient element 111 formed of a material arranged to resiliently deform or compress and expand in a direction along the axle 108. The spacer unit 110 can thus axially compress or expand to controllably vary a thickness T of the spacer unit 110 to fit the gap G and other gaps having differing sizes without labor- and cost-intensive grinding and/or other adjustments. The spacer unit 110 further can provide axial resistance arranged to help space the first component 102 from the second component 104.

If the gap G is smaller, the spacer unit 110 can compress more axially to fill the gap G. If the gap G is larger, the spacer unit 110 can compress less axially or compress and then expand axially to fill the gap G. This beneficially allows the spacer unit 110 to accommodate or absorb differences in gap widths or sizes without having to modify washers or add more washers in the gap as in the prior art, providing a simpler and less labor-intensive assembly of the movable joint 100. The thickness T of the spacer unit 110 can be variable during the use of the movable joint 100. For instance, it can dynamically reduce axial play between the first and second components 102, 104 during use of the movable joint 100 as the thickness T of the spacer unit 110 changes with the gap size while helping to maintain the first and second components 102, 104 apart. In an embodiment, the spacer unit 110 can be arranged to resiliently compress and/or expand between about 1% and about 80% in the axial direction. For instance, when compressed in the movable joint 100, the thickness T or length of the spacer unit 110 along an axis 113 can be arranged to be about 95%, about 90%, about 85%, or about 80% of its original thickness T or length. In other words, the thickness T or length of the spacer unit 110 along the axis 113 can be arranged to reduce by about 5%, about 10%, about 15%, or about 20% when the spacer unit 110 is compressed in the movable joint 100.

The compression and/or pre-compression of the resilient element 111 is at least in part dependent on stiffness and/or density of the material included in the resilient element 111 and can vary for different types of material. As such, different materials forming the resilient element 111 can be selected to achieve the desired compression of the spacer unit 110 for specific applications. For example, a denser foam material or elastomer material can be selected such that the spacer unit 110 exhibits less compression in the axial direction, which, in turn, increases the resistance of the spacer unit 110 to relative movement between the first and second components 102, 104. Or, a less stiff foam material or elastomer material can be selected such that the spacer unit 110 exhibits more compression in the axial direction.

In addition to overcoming free play between the components 102, 104, the spacer unit 110 may provide an amount of axial damping to the movable joint 100. By way of example, when the movable joint 100 is loaded axially, the resilient element 111 can deform between the first and second components 102, 104 to extract mechanical energy from axial movement between the first and second components 102, 104, which, in turn, provides an amount of axial damping in the movable joint 100.

The spacer unit 110 may also provide an amount of torsional damping to the prosthetic system 10. The resilient element 111 can be twistable in a gap G1 located between first and second components 102, 104 to provide an amount of torsional damping during use of the movable joint 100. When there is relative rotation between the first and second components 102, 104, at least part of the resilient element 111 can resiliently twist and deform to extract mechanical energy from the rotational movement between the first and second components 102, 104, which, in turn, provides an amount of torsional damping in the movable joint 100. Such damping from the spacer unit 110 can enhance user comfort and safety and helps the movement of the movable joint 100 feel more natural. In an embodiment, the amount of damping provided by the spacer unit 110 can be controlled by the size and/or material of the spacer unit 110. For instance, an increase in the thickness T of the spacer unit 110 or a selected material forming the resilient element 111 can provide a greater amount of axial damping. According to a variation, the resilient element 111 is arranged to provide an amount of controlled resistance to rotation between the first and second components 102, 104, helping to control the movement of the prosthetic system 10. The first component 102 can be a housing or upper knee part and the second component 104 can be at least one link connecting the first component 102 to a chassis or lower knee part.

In an embodiment, the resilient element 111 includes an anisotropic material arranged to resiliently compress in the first direction (e.g., axial direction) with little or no change in shape in the second direction (e.g., radial direction). The spacer unit 110 can thus be arranged for applications where the surrounding space is confined or where the spacer unit 110 is located within an enclosure or groove. For instance, the spacer unit 110 can be received in the gap G1 within a bushing or sleeve 112 as shown in FIG. 3. The anisotropic material of the resilient element 111 can be a resiliently compressible material, a foam material, an open-celled material, an elastomer material, combinations thereof, or any other suitable anisotropic material. The anisotropic material is preferably a polyurethane foam material such as Cellasto from BASF.

When the first and second components 102, 104 are loaded axially, the spacer unit 110 can be compressed between the first and second components 102, 104 as the gap G1 is reduced to gap G2, having a smaller size. As the spacer unit 110 is axially compressed, the diameter D or radial dimension of the spacer unit 110 can be substantially unchanged. When the first and second components 102, 104 are unloaded axially, stored energy in the resilient element 111 can cause the spacer unit 110 to expand axially between the first and second components 102, 104 without substantially changing shape in a radial direction as the gap G2 returns toward the gap G1. This permits the spacer unit 110 to absorb differences or changes in gap sizes and reduce free play between the components 102, 104 without engaging or interfering with the sleeve or bushing 112 in the radial direction, improving performance and safety of the movable joint 100. In an embodiment, the spacer unit 110 is arranged to compress and/or expand between about 10% and about 25% (e.g., 20%) or between about 15% and about 20% in the axial direction without substantially changing shape in a radial direction.

It will be appreciated that the spacer unit of the present disclosure is advantageous over known movable joints in prosthetic systems that have attempted to use elastomeric washers in gaps between joint components. Such washers exhibit relatively large radial expansion when compressed and are thus prone to engage and interfere with the movable joint in the radial direction. This detrimentally can cause the movable joint to bind or fail and presents a serious threat of injury to a user.

The advantages described above are only some of those provided by the spacer unit of the present disclosure. For example, the spacer unit 110 can have a lightweight and durable configuration, reducing the overall weight and increasing the overall durability of the prosthetic system 10. In other embodiments, the spacer unit 110 can also reduce the likelihood of a slip-stick effect in the movable joint 100. Slip-stick effect is generally the spontaneous jerking motion that can occur while two components slide over each other. In the movable joint 100, the static coefficient of friction between a rigid washer (metal and plastic) and at least one of the components 102, 104 can be greater than the kinetic coefficient of friction. If a rotational force between the washer and component is large enough to overcome the static friction, then the reduction of the friction to the kinetic friction can cause a sudden jump in the velocity of the movement, which can be highly disruptive to a user when walking or standing.

When the spacer unit 110 is used in the movable joint 100, the differential between the static and kinetic coefficients at the interface between the resilient element 111 of the spacer unit 110 and at least one of the components 102, 104 can be less than between a plastic or metal washer and the components 102, 104. As a result, when at least one of the components 102, 104 rotate over the spacer unit 110, the friction reduction therebetween is less, which, in turn, reduces the likelihood and magnitude of a sudden increase in velocity of the first component 102 and/or the second component 104. Moreover, when at least one of the first and second components 102, 104 rotates over the spacer unit 110, the resilient element 111 can twist and rotate with the at least one of the components 102, 104, reducing the slip-stick effect in the movable joint 100. In other embodiments, the resilient element 111 can reduce vibrations within the movable joint 100.

According to a variation, the resilient element is formed of a foam material such as a polyurethane foam or an open-celled material. The resilient element 111 can include a heat formable material. In other embodiments, the resilient element 111 can include ethylene-vinyl acetate (EVA) foam and/or thermoplastic elastomers (TPE). The resilient element 111 can include an elastomeric material. The materials and construction of the spacer unit described are to be regarded as exemplary only, as any suitable materials and/or properties that can structurally fill the gap and dampen the movable joint may be envisioned.

FIG. 4 shows a spacer unit 210 according to another embodiment. The spacer unit 210 includes at least one rigid element 220 and a resilient element 222 resiliently compressible and expandable to controllably vary a thickness of the spacer unit 210 to fit the gap of a movable joint. The spacer unit 210 also can provide an axial resistance arranged to help space a first component of the movable joint from a second component. In an embodiment, the resilient element 222 includes an anisotropic material that can resiliently compress in the first direction (e.g., axial direction) with little or no change in shape in the second direction (e.g., radial direction). This beneficially permits the spacer unit 210 to absorb differences or changes in gap size without interfering with a movable joint in a radial direction. The anisotropic material can comprise a polyurethane foam material.

The resilient element 222 and the at least one rigid element 220 can be in a stacked configuration. For instance, the at least one rigid element 220 can comprise a pair of outer rigid elements 220 and the resilient element 222 can be located between the outer rigid elements 220. The resilient element 222 may be fixedly attached to the outer rigid elements 220 or the resilient element 222 may be connected to the outer rigid elements 220 such that some degree of relative movement is allowed between the resilient element 222 and the outer rigid elements 220. The outer rigid elements 220 can have the same or different thicknesses. At least one of the outer rigid elements 220 can have a substantially same shape of the resilient element 222.

In use, the outer rigid elements 220 can form bearing surfaces between the spacer unit 210 and components of the movable joint and the resilient element 222 can resiliently compress between the outer rigid elements 220 to absorb differences or changes in gap sizes and reduce free play between the components of the movable joint. This allows the spacer unit 210 to compress and distribute loads in the gap, reducing wear and tear on the spacer unit 210. For instance, the outer rigid elements 220 direct forces away from the resilient element 222 while the resilient element 222 dampens axial and torsional movement of the movable joint and reduces free play between the components.

FIG. 5 shows a spacer unit 310 according to another embodiment including a rigid element 320 and a resilient element 322 resiliently compressible and expandable to controllably vary a thickness of the spacer unit 310 to fill or fit the gap of a movable joint. The resilient element 322 may include an anisotropic material arranged to resiliently compress in the first direction (e.g., axial direction) with little or no change in shape in the second direction (e.g., radial direction).

The resilient element 322 defines a first surface attached to the rigid element 320 and a second surface arranged to interact with the movable joint. This allows the rigid element 320 to distribute loads away from the resilient element 322 and the resilient element 322 to reduce stick-slip motion in the movable joint. The rigid element 320 and the resilient element 322 can have the same or different diameters or lateral dimensions. The rigid element 320 and the resilient element can have a substantially same shape.

FIG. 6 shows a spacer unit 410 according to yet another embodiment. The spacer unit 410 includes a rigid element 420, a first resilient element 422 attached to the rigid element 420 and including a first anisotropic material, and a second resilient element 424 attached to the first resilient element 422 and including a second anisotropic material. The first and second resilient elements 422, 424 can have a same or different thickness. The first and second anisotropic materials can be different materials. The first and second anisotropic materials can be a foam material, TPE, EVA, or any other suitable material. The resiliency, resistance, compressibility, and/or other properties of the spacer unit 410 may vary from resilient element to resilient element. Differences between the first and second resilient elements 422, 424 can be selected to vary their characteristics during movement of the movable joint. For instance, the first and second resilient elements 422, 424 can be arranged to compress or deform differently or progressively under different conditions.

Spacer unit embodiments described herein can be in any suitable form for use in a movable joint. For instance, FIG. 7 shows a spacer unit 510 having an annular shape defining a central opening 512 for receiving an axle, shaft, or pin of a movable joint. FIG. 8 shows a spacer unit 610 in the form of a strip element. The spacer unit 610 can be wrapped or extended around an axle, shaft, or pin in a gap. FIG. 9 shows a spacer unit 710 having a C-shape that can be slid onto an axle, a shaft, or a pin from a radial direction.

Figure 10:
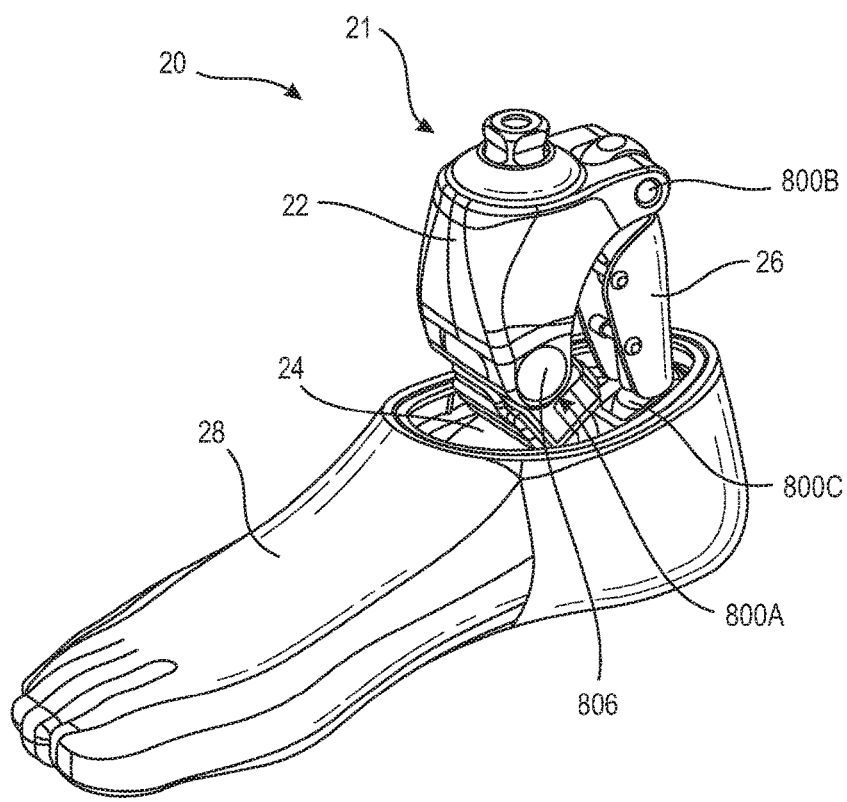
FIG. 10 is a perspective view of a prosthetic device including a movable joint according to another embodiment.
Figure 11:
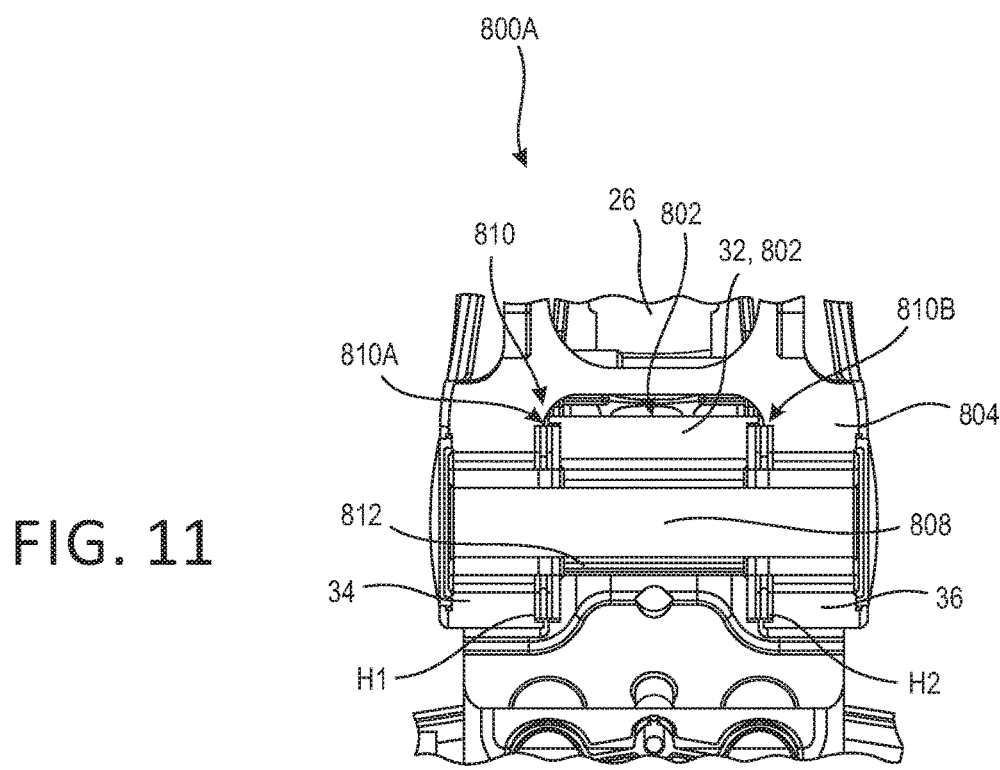
FIG. 11 is a cross-section of a movable joint in FIG. 10.

FIGS. 10 and 11 illustrate a prosthetic system 20 according to another embodiment comprising a prosthetic foot 21 including a plurality of movable joints with at least one spacer unit 810. The prosthetic foot 21 has an ankle unit 22. The ankle unit 22 is pivotally connected to a foot element 24 at a first movable joint 800A along the front of the ankle unit 22 and to a connection member 26 at a second movable joint 800B that is located at a rear portion of the prosthetic foot 21.

The connection member 26 is connected to a rear of the foot element 24 at a third movable joint 800C and connects the ankle unit 22 and the rear of the foot element 24. The connection member 26 can be in a variety of forms such as a connection member, an actuator, a rod connector, a rigid member, or a piston cylinder. The connection member 26 can be operated in a variety of ways, as described by example, in U.S. Pat. No. 7,896,927 and U.S. patent application Ser. No. 12/816,968, each of which is incorporated herein by reference in its entirety.

In use, the prosthetic foot 21 can expand and compress. The prosthetic foot 21 is in expansion when the ankle unit 22 rotates in a counter-clockwise direction about the first movable joint 800A and the connection member 26 pushes the rear portion of the foot element 24 toward an underlying heel element (not shown). The prosthetic foot 21 is in compression when the ankle unit 22 rotates in a clockwise direction about the first movable joint 800A and the connection member 26 pulls the rear portion of the foot element 24 upwardly away from the heel element. The prosthetic foot 21 may be insertable into a foot cover 28 as seen in FIG. 10. An example of the prosthetic foot 21 is described in greater detail in U.S. Pat. No. 9,561,118, and commercially available as the PRO-FLEX by Ossur. This disclosure is incorporated by reference and belongs to the assignee of this disclosure.

Spacer units of the present disclosure can be adapted for use in one or more of the movable joints 800A, 800B, or 800C to facilitate assembly, reduce free play in the movable joint, and/or improve the performance of the movable joint. For instance, FIG. 11 is a cross-section through the movable joint 800A. The movable joint 800A includes a first component 802 comprising an attachment portion 32 of the foot element 24. The first component 802 can include or define a bushing 812 or opening through which an axle 808 extends. A second component 804 of the movable joint 800A is formed by the lower portion of the ankle unit 22. The second component 804 accommodates the axle 808 and receives the first component 802 between a pair of flanges 34, 36. The first and/or second components 802, 804 can rotate a pivot point 806 defined by the axle 808.

As shown in FIG. 11, the movable joint 800A includes a first gap H1 defined between the first component 802 and the flange 34, and a second gap H2 defined between the first component 802 and the flange 36. A first spacer unit 810A is located in the first gap H1 and a second spacer unit 810B is located in the second gap H2.

The spacer units 810A, 810B can be configured similarly to any of the spacer unit embodiments described herein, such as by including at least one resilient element formed of an anisotropic material arranged to accommodate or absorb differences in size of the gaps H1, H2 with little or no radial expansion. The spacer units 810A, 810B also provide an axial resistance arranged to help space the first component 802 and the second component 804. This provides a simpler and less labor-intensive assembly of the movable joint 800A and reduces axial play between the first and second components 802, 804 without interfering with the movable joint 800A. The spacer units 810A, 810B also can provide an amount of torsional damping as the first and second components 802, 804 rotate relative to one another, making the movement of the movable joint 800A feel more natural or smooth. Moreover, the spacer units 810A, 810B can offer an amount of axial damping if lateral or medial forces are generated within the movable joint 800A.

In the illustrated embodiment, the spacer units 810A, 810B can include one or more rigid elements and at least one resilient element. For instance, the spacer units 810A, 810B can include a first rigid element formed of metal, a second rigid element formed of plastic, a third rigid element formed of metal, and the resilient element formed of an anisotropic material. The first and third rigid elements can be made of stainless steel or other suitable metal material. This allows the rigid elements to direct forces away from the resilient element and allows the resilient element to compress and absorb differences or changes in the size of the gaps H1 or H2. Further, because the resilient element can compress with little or no expansion in the radial direction, the spacer units 810A, 810B are less likely to interfere with relative rotation between the ankle unit 22 and the foot element 24. Moreover, the rigid elements formed of the metal provide a hard contact surface between the spacer unit and the movable joint to help to provide less wearing in the spacer units 810A, 810B, which, in turn, provides greater stability and safety to a user.

In other embodiments, the spacer units 810A, 810B can include any number and or type of elements such as a first rigid element comprising a first metal washer, a second rigid element comprising a second metal washer, and the resilient element comprising an anisotropic foam washer positioned between the first and second rigid elements. In yet other embodiments, at least one of the spacer units 810A, 810B can include a first rigid element formed of plastic, a second rigid element formed of metal adjacent to the first rigid element, and the resilient element formed of an anisotropic material adjacent to the second rigid element. Again, this allows the rigid elements to direct forces away from the resilient element and allows the resilient element to compress and absorb differences or changes in the size of the gaps H1 or H2. The reduction of parts forming the spacer unit can also help reduce the overall size and weight of the spacer unit 810A and/or the spacer unit 810B.

Figure 12:
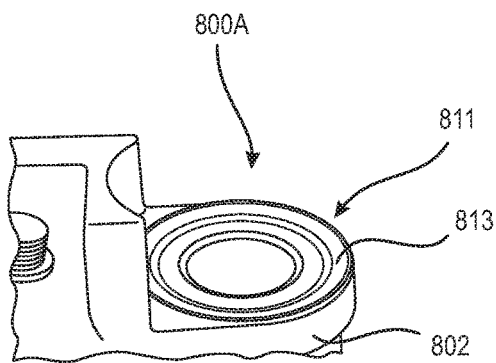
FIG. 12 is a partial exploded view of the movable joint in FIG. 1.

According to a variation shown in FIG. 12, at least one of the rigid elements 811 can define a groove 813 sized and configured to help maintain the position of the resilient element within the spacer unit 810A or 810B and/or the gaps H1 or H2.

Figure 13:
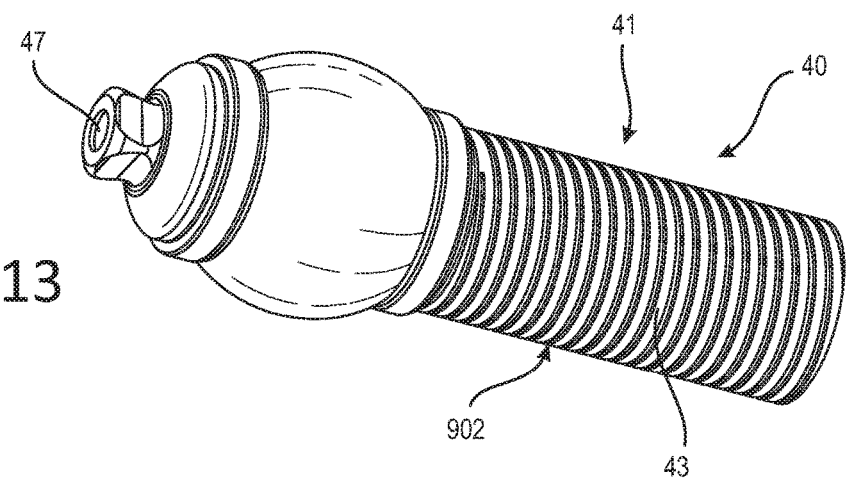
FIG. 13 is a perspective view of a prosthetic device including a movable joint according to another embodiment.
Figure 14:
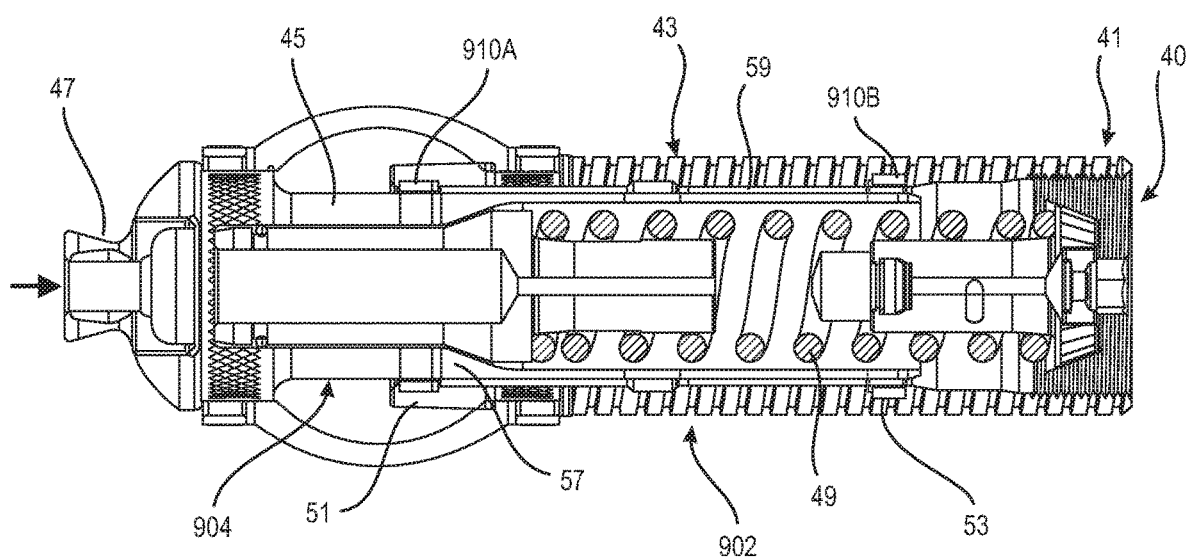
FIG. 14 is a cross-section of the prosthetic device in FIG. 13.

FIGS. 13 and 14 illustrate a prosthetic system 40 according to yet another embodiment comprising a shock absorber 41 arranged to provide shock absorption to a prosthetic foot. The shock absorber 41 includes a first component 902 comprising an outer tube 43 and a second component 904 comprising an inner tube 45 and/or bushing 57 that guides movement of the inner tube 45 within the outer tube 43. The inner tube 45 is operatively connected to a male pyramid 47 and a spring element 49 housed within the shock absorber 41. When the shock absorber 41 is loaded and compressed during stance, the inner tube 45 slides toward a bottom of the outer tube 43, which, in turn, compresses the spring element 49. When the shock absorber is unloaded and decompressed, stored energy or spring force in the spring element 49 forces the inner tube 45 and the male pyramid 47 back toward their original position.

The inner surface of the outer tube 43 defines a first gap comprising a first annular groove 51 toward the male pyramid 47 and a second gap comprising a second annular groove 53 toward a bottom of the outer tube 43. A first spacer unit 910A is positioned in the first annular groove 51 and a second spacer unit 910B is positioned in the second annular groove 53. In other embodiments, the spacer units can be positioned in annular grooves formed in the outer surface of the inner tube 45.

The first and second spacer units 910A, 910B comprise resilient elements in the form of strip elements extending circumferentially around the inner surface of the outer tube 43. The strip elements can be disposed in the first and second annular grooves 51, 53 such that a small or no gap remains between the ends of the strip elements. Like other embodiments, the resilient elements are arranged to resiliently compress and expand in the first and second annular grooves 51, 53. This helps the resilient elements fit in the grooves and reduce play between at least the outer tube 43 and the bushing 57, simplifying assembly of the shock absorber 41 and improving performance. This is beneficial because the bushing 57 and other bushings are known to vary in size due to manufacturing imperfections and have generally required labor-intensive practices to ensure a proper fit in prosthetic shock absorbers. The resilient elements also provide an axial resistance arranged to help space the first component 902 and the second component 904.

According to a variation, at least one of the resilient elements can include an anisotropic material that can compress in a first direction with little or no change in shape in a second direction normal to the first direction, reducing the likelihood of the resilient element interfering with relative movement between the first and second components 902, 904.

In addition, an engagement between the spacer units 910A, 910B and the bushing 57 can reduce the likelihood of a stick-slip effect during use of the shock absorber 41. The spacer units 910A, 910B can also provide an amount of damping in the axial and/or torsional direction. In an embodiment, the damping provided by the spacer units 910A, 910B can be adjustable to isolate or vary the spring force provided by the spring element 49. For instance, a dimension of the spacer units 910A, 910B (e.g., a length or thickness) can be selected to isolate the amount of damping provided by the spacer units 910A, 910B from the spring force provided by the spring element 49. In other embodiments, a dimension of the spacer units 910A, 910B can be selected to isolate the amount of damping provided by the spacer units 910A, 910B from bushing 57 guiding movement of the inner tube 45.

Optionally, the spacer units 910A, 910B can be resistant to lubricant such as grease. This allows the spacer units 910A, 910B to keep grease or other lubricants within a chamber 59 defined within the outer tube 43 and along a length between the spacer units 910A, 910B. This is advantageous over known shock absorbers that have a substantially smaller volume (e.g., a single annular groove) for carrying lubricant. As such, the spacer units 910A, 910B help increase the lubricant capacity of the shock absorber 41, improving lubrication and reducing wear and tear during the life cycle of the shock absorber 41. Further, the resilient elements are arranged to recover and resist permanent deformation after being compressed over and over during the life cycle of the shock absorber 41, helping to prevent lubricant from undesirably leaking through the spacer units 910A, and 910B. This also helps the resilient elements eliminate free play between the bushing 57 and the outer tube 43 over the life cycle of the shock absorber 41.

The spacer units 910A, 910B can also be air permeable such that air can be expelled from the shock absorber 41 via the spacer units 910A, 910B during compression of the shock absorber 41. For instance, the spacer units 910A, 910B can be arranged so that air can move between the ends of the strip elements in the first and second annular grooves 51, 53. In other embodiments, the spacer units 910A, 910B can be arranged so that air can move through flow paths defined in the structure of the spacer units 910A, 910B ensuring smoother operation of the absorber.

Figure 15:
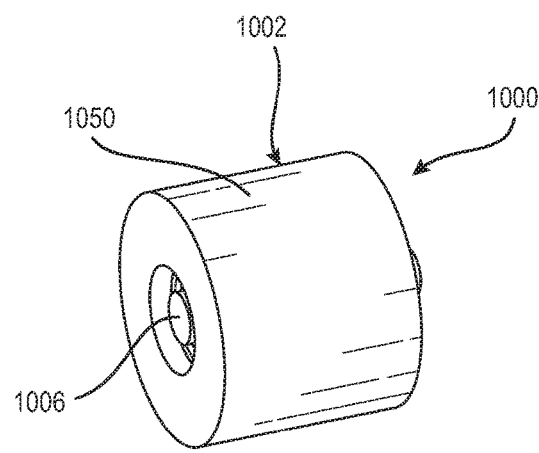
FIG. 15 is a perspective view of a movable joint according to another embodiment.
Figure 16B:
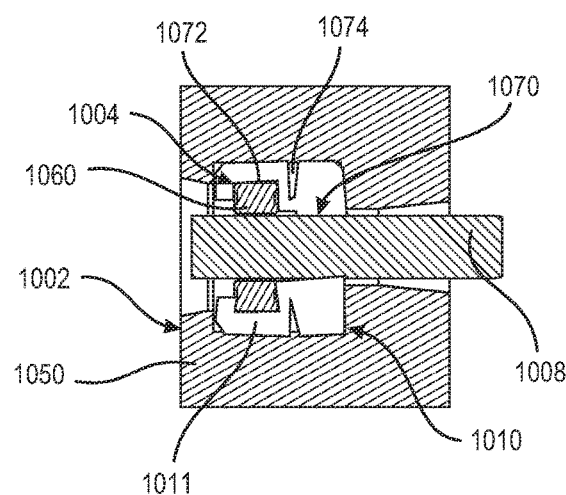
FIG. 16B is another cross-section of the movable joint in FIG. 15.
Figure 16A:
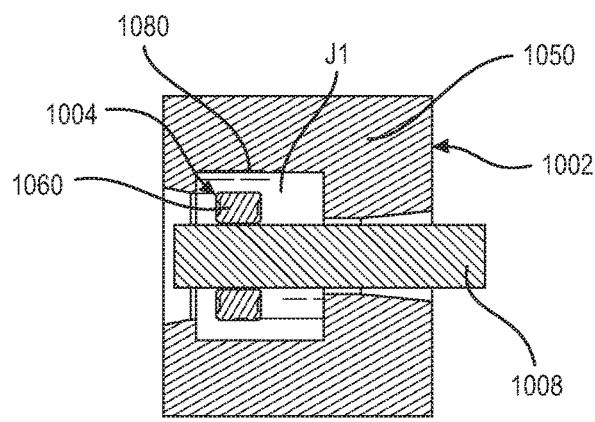
FIG. 16A is a cross section of the movable joint in FIG. 15.
Figure 17:
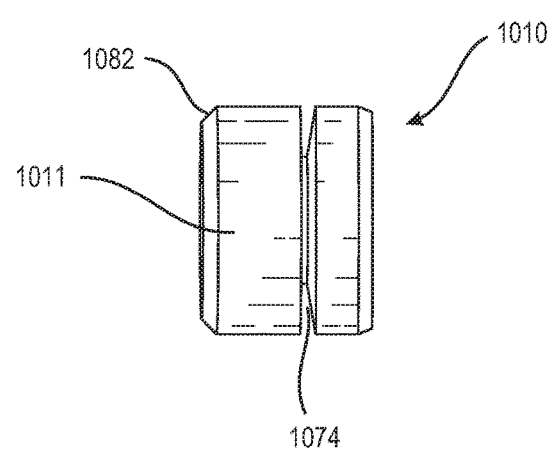
FIG. 17 is a side view of the spacer unit in FIG. 16A.

FIGS. 15-17 illustrate yet another embodiment of a movable joint 1000 for use in a prosthetic or orthopedic system. The movable joint 1000 comprises a bearing assembly including a first component 1002 and a second components 1004 which are arranged to rotate relative to one another about at least one pivot point 1006. The pivot point 1006 is defined by an axle or shaft 1008 extending through the first and second components 1002, 1004. The first component 1002 comprises a housing 1050 and the second component comprises a bearing 1060 that movable couples the housing 1050 to the shaft 1008. The movable joint 1000 can be incorporated in a prosthetic foot, a prosthetic ankle, a prosthetic knee, or any suitable prosthetic or orthopedic system. As shown best in FIG. 16A, a gap J1 is defined between the bearing 1060 and the housing 1050. The gap J1 extends in the radial direction between the bearing 1060 and the housing 1050 and on both sides of the bearing 1060 in the axial direction.

Referring now to FIGS. 16B and 17, a spacer unit 1010 is insertable in the gap J1 to help maintain the fit between the housing 1050 and the bearing 1060 and position the shaft 1008 and bearing 1060 within the housing 1050. It will be appreciated that the spacer unit 1010 can incorporate any of the features described herein. The spacer unit 1010 includes a resilient element 1011 resiliently compressible and expandable to controllably vary a thickness of the spacer unit to fill or fit the gap J1.

In an embodiment, the resilient element 1011 can include an anisotropic material arranged to axially compress or expand in the axial direction to fill the gap J1 with little no change in shape in the radial direction. This allows the spacer unit 1010 to accommodate or absorb changes in the size of the gap J1 in the axial direction and reduce free play between the bearing 1060 and the housing 1050 in both the radial and axial directions. Moreover, the spacer unit 1010 can do so without undesirably interfering with the bearing 1060 and/or housing 1050 in the radial direction, facilitating assembly of the movable joint 1000 and improving its performance.

The spacer unit 1010 can also provide an amount of impact damping to the movable joint 1000. For instance, when the housing 1050 is loaded or impacted axially, the resilient element 1011 can deform between the housing 1050 and the bearing 1060 to extract mechanical energy from axial movement between the housing 1050 and the bearing 1060, which, in turn, provides axial damping and helps protect the bearing 1060 from impact loads on the movable joint 1000 along the shaft 1008. When the housing 1050 is loaded or impacted radially relative to the shaft 1008, the spacer unit 1010 can be arranged to deform between the housing 1050 and the bearing 1060 to extract mechanical energy from radial movement between the housing 1050 and the bearing 1060, which, in turn, provides radial damping and likewise helps protect the bearing 1060 from non-axial impact loads on the movable joint 1000. This helps improve the operational life of the bearing 1060 and movable joint 1000.

The spacer unit 1010 may also provide an amount of torsional damping to the movable joint 1000. When there is relative rotation between the housing 1050 and at least part of the bearing 1060, at least part of the spacer unit 1010 may resiliently twist and deform to extract mechanical energy from the rotational movement between the housing 1050 and the bearing 1060, which, in turn, provides an amount of torsional damping in the movable joint 1000. According to a variation, the spacer unit 1010 can be arranged to provide more motion along a helical axis. For instance, as the resilient element 1011 rotates or twist about the shaft 1008 or its axis of rotation with the housing 1050, at least a portion of the spacer unit 1010 can be arranged to translate a distance along the shaft 1008. By varying the shape and/or properties of the resilient element 1011, the amount of rotation and/or translation can be controlled to help define movement within the movable joint 1000. For instance, the spacer unit 1010 can be arranged to help the movable joint 1000 more closely follow the natural movement of a limb between different poses (e.g., extreme plantarflexion to extreme dorsiflexion).

Referring to FIGS. 16B and 17, the spacer unit 1010 can have any suitable shape but is shown having a cylindrical shape arranged to fit within a receiving space 1080 formed in the housing 1050. The spacer unit 1010 defines a central opening 1070 arranged to receive the shaft 1008, allowing the spacer unit 1010 to be carried on the shaft 1008 within the housing 1050. The central opening 1070 includes an annular groove 1072 that receives and fits over the bearing 1060, a first diameter on one side of the annular groove 1072 generally corresponding to an outer diameter of the shaft 1008 and a second diameter on the other side of the annular groove 1072 that is greater than the outer diameter of the shaft 1008. The second diameter is oversized relative to the shaft 1008. This advantageously helps heat more easily dissipate from the bearing 1060 and facilitates visual inspection of the bearing 1060 within the housing 1050.

The outer surface of the spacer unit 1010 includes a circumferential groove 1074 extending entirely about the body of the spacer unit 1010 and terminating a radial distance from the central opening 1070. By varying the depth, shape, and or width of the groove 1074, the compressibility, stiffness, torsional resistance, damping and/or movement of the spacer unit 1010 can be controlled. For instance, the groove 1074 can help isolate movements within the spacer unit 1010 by providing a clearance to accommodate or facilitate movement of the portion of the spacer unit 1010 engaging the bearing 1060 relative to the portion of the spacer unit 1010 engaging or adjacent the shaft 1008. This advantageously can help increase the amount of damping provided by the spacer unit 1010. The resilient element 1011 can be formed of polyurethane foam, TPE, EVA, or any other suitable material.

Optionally, the outer surface of the spacer unit 1010 can include at least one chamfered edge 1082 to help prevent edge loading or stress concentrations on the spacer unit 1010 within the receiving space 1080 of the housing 1050. The movable joint 1000 is shown including one bearing; however, it will be appreciated that the movable joint could have two, three, or any suitable number of bearings and the spacer unit or spacer units can be arranged to accommodate the same.

While various aspects and embodiments have been disclosed herein, other aspects and embodiments are contemplated. For instance, while the resilient element embodiments are described to resiliently compress in a first direction (e.g., axial direction) with little or no expansion in a second direction normal to the first direction (e.g., radial direction), in other embodiments, the resilient element may compress differently in the first and second directions. In an embodiment, the resilient element may be arranged to resilient compress in the radial direction with little or no expansion in the axial direction.

The disclosed embodiments and variations thereof overcome the problems of prosthetic devices being labor- and cost-intensive to produce because of ill-fitting components such as metal washers that need to be ground down to size or outfitted with additional washers. The embodiments also address the problem of stick/slip effects in moving parts in prosthetics by providing a resilient element in a spacer unit. The embodiments also provide an improved system that provides axial and radial damping effects for improved comfort in prosthetic devices.

The various aspects and embodiments disclosed herein are for purposes of illustration and are not intended to be limiting. Additionally, the words "including," "having," and variants thereof (e.g., "includes" and "has") as used herein, including the claims, shall be open-ended and have the same meaning as the word "comprising" and variants thereof (e.g., "comprise" and "comprises").

The invention claimed is:

1. A prosthetic system comprising:
   a movable joint defining at least one gap; and
   at least one spacer unit positionable in the at least one gap, the at least one spacer unit including a resilient element formed of at least one material that is controllably deformable to vary a thickness of the at least one spacer unit to fill the at least one gap, and to reduce a likelihood of the at least one spacer unit interfering with relative movement between first and second components of the movable joint, wherein the at least one material forming the resilient element is configured to compress in a first direction with little or no expansion in a second direction normal to the first directions;
   wherein the at least one gap is axially defined between the first and second components;
   wherein an axle extends through the first and second components and entirely through the spacer unit, such that the first and second components are arranged to rotate about the axle and move relative to one another;
   wherein the spacer unit has an axis along which a central opening is defined, the spacer unit is coaxial to the axle such that the thickness varies along the axis.

2. The prosthetic system of claim 1, wherein the at least one material forming the resilient element is a foam material.

3. The prosthetic system of claim 1, wherein the at least one material forming the resilient element is an elastomeric material.

4. The prosthetic system of claim 1, wherein the at least one material forming the resilient element is configured to reduce a differential between a static coefficient of friction and a kinetic coefficient of friction at an interface between the at least one spacer unit and the movable joint.

5. The prosthetic system of claim 1, wherein the thickness of the at least one spacer unit is variable during use of the movable joint to accommodate changes in a width of the at least one gap.

6. The prosthetic system of claim 1, wherein the resilient element is compressible in the at least one gap to provide an amount of axial damping to the movable joint when the movable joint is loaded along an axis of the movable joint.

7. The prosthetic system of claim 6, wherein the resilient element is twistable in the at least one gap to provide an amount of torsional damping to the movable joint when at least part of the movable joint rotates about the axis.

8. The prosthetic system of claim 1, wherein the at least one spacer unit includes at least one rigid element forming a bearing surface between the at least one spacer unit and the movable joint to direct forces away from the resilient element.

9. The prosthetic system of claim 8, wherein the at least one rigid element and the resilient element have a substantially same shape.

10. The prosthetic system of claim 8, wherein the least one rigid element and the resilient element have an annular shape.

11. The prosthetic system of claim 8, wherein the at least one rigid element comprises a first rigid element, a second rigid element, and the resilient element is positioned between the first rigid element and the second rigid element.

12. The prosthetic system of claim 11, wherein the resilient element is twistable between the first rigid element and the second rigid element to provide an amount of torsional damping to the movable joint.

13. The prosthetic system of claim 11, wherein the resilient element is compressible between the first rigid element and the second rigid element to provide an amount of axial damping to the movable joint when the movable joint is loaded in an axial direction.

14. The prosthetic system of claim 8, where the resilient element is attached to the at least one rigid element so that a degree of relative is allowed between the resilient element and the at least one rigid element.

15. The prosthetic system of claim 1, wherein the first and second components and the spacer unit are received in a sleeve, the spacer unit is arranged to absorb differences or changes in gap sizes and reduce play between the components without engaging or interfering with the sleeve in a radial direction.

* * * * *